United States Patent
Braun

(10) Patent No.: US 9,633,578 B2
(45) Date of Patent: Apr. 25, 2017

(54) METHODS AND SYSTEMS FOR TRACKING OCCURRENCES AND NON-OCCURRENCES OF MEDICAL-RELATED EVENTS

(71) Applicant: Lauren R. Braun, Indianapolis, IN (US)

(72) Inventor: Lauren R. Braun, Indianapolis, IN (US)

(*) Notice: Subject to any disclaimer, the term of this patent is extended or adjusted under 35 U.S.C. 154(b) by 0 days.

(21) Appl. No.: 14/030,462

(22) Filed: Sep. 18, 2013

(65) Prior Publication Data
US 2014/0013638 A1    Jan. 16, 2014

Related U.S. Application Data

(63) Continuation of application No. 13/662,664, filed on Oct. 29, 2012, now abandoned, which is a continuation of application No. PCT/US2011/033967, filed on Apr. 26, 2011.

(60) Provisional application No. 61/328,514, filed on Apr. 27, 2010.

(51) Int. Cl.
| | | |
|---|---|---|
| G09F 3/00 | (2006.01) | |
| G09F 3/02 | (2006.01) | |
| A61B 90/90 | (2016.01) | |
| A61B 90/94 | (2016.01) | |
| A61B 17/20 | (2006.01) | |
| A61B 90/00 | (2016.01) | |

(52) U.S. Cl.
CPC ............ *G09F 3/005* (2013.01); *A61B 90/90* (2016.02); *A61B 90/94* (2016.02); *G09F 3/00* (2013.01); *G09F 3/02* (2013.01); *A61B 17/20* (2013.01); *A61B 2090/0803* (2016.02)

(58) Field of Classification Search
CPC ......................................................... G09F 3/005
USPC ............................................................ 40/633
See application file for complete search history.

(56) References Cited

U.S. PATENT DOCUMENTS

| | | | | |
|---|---|---|---|---|
| 2,528,259 | A | | 10/1950 | Annunziata |
| 3,675,620 | A | * | 7/1972 | Baustin ................. A61J 7/04 116/308 |
| 5,704,067 | A | * | 1/1998 | Brady ................... G09F 3/005 116/222 |
| 6,880,364 | B1 | | 4/2005 | Vidolin et al. |

(Continued)

OTHER PUBLICATIONS

International Application No. PCT/US2011/033967 International Search Report and Written Opinion, mailed Feb. 8, 2012.

*Primary Examiner* — Gary C Hoge
(74) *Attorney, Agent, or Firm* — Maurer School of Law, Indiana University

(57) ABSTRACT

Described in some aspects of the present invention are methods and systems that can be used to track occurrences and/or non-occurrences of medical-related events, for example, to record whether one or more medical-related events have occurred at a particular time or during a particular time interval. Any suitable number of events may be tracked using such methods and systems, and the types and varieties of events that can be tracked are diverse. Examples include but are not limited to vaccine or other drug administrations, physical therapies, tests, diagnoses and surgeries. In some preferred embodiments, these and/or other medical-related occurrences or events will be tracked using an article that can be worn about the body of a patient although a variety of non-wearable articles can be utilized as well.

16 Claims, 5 Drawing Sheets

(56) References Cited

U.S. PATENT DOCUMENTS

| | | | |
|---|---|---|---|
| 7,331,707 B2 * | 2/2008 | DelValle | A44C 5/0015 |
| | | | 116/308 |
| 7,481,370 B2 * | 1/2009 | Davis | A61B 5/117 |
| | | | 235/375 |
| D591,633 S * | 5/2009 | Del Valle | D11/3 |
| 7,542,379 B2 | 6/2009 | Kimel et al. | |
| D617,231 S | 6/2010 | Adamson | |
| 7,942,674 B2 | 5/2011 | Murphy | |
| 8,040,668 B1 | 10/2011 | Alkire, III | |
| 2003/0111005 A1 | 6/2003 | Lord et al. | |
| 2005/0091896 A1 * | 5/2005 | Kotik | G06F 19/323 |
| | | | 40/633 |
| 2007/0297293 A1 | 12/2007 | DelValle et al. | |
| 2008/0010874 A1 * | 1/2008 | Londino | A61J 7/04 |
| | | | 40/310 |
| 2008/0028654 A1 * | 2/2008 | Cardon | G09F 3/005 |
| | | | 40/633 |
| 2008/0266118 A1 | 10/2008 | Pierson et al. | |
| 2009/0265971 A1 * | 10/2009 | Cook | G09F 3/005 |
| | | | 40/633 |
| 2010/0132237 A1 * | 6/2010 | McDermott | G09F 3/005 |
| | | | 40/633 |
| 2010/0237115 A1 * | 9/2010 | Booker | A44C 5/0023 |
| | | | 224/267 |
| 2011/0185606 A1 * | 8/2011 | Londino | A61J 7/04 |
| | | | 40/310 |
| 2012/0186121 A1 * | 7/2012 | Hanssen | A44C 5/0053 |
| | | | 40/633 |

* cited by examiner

METHODS AND SYSTEMS FOR TRACKING OCCURRENCES AND NON-OCCURRENCES OF MEDICAL-RELATED EVENTS

CROSS-REFERENCE TO RELATED APPLICATIONS

This application is a continuation of U.S. patent application Ser. No. 13/662,664, filed Oct. 29, 2012, which is a continuation of International Patent Application No. PCT/US2011/033967, filed Apr. 26, 2011, which claims the benefit of U.S. Provisional Patent Application No. 61/328,514, filed Apr. 27, 2010, which are hereby incorporated by reference.

BACKGROUND

The present invention relates generally to medical technology and in particular aspects to wearable articles and related methods and systems for tracking whether one or more medical-related events have occurred.

As further background, children in developing countries are much more likely to survive childhood if they receive immunizations in a timely manner. If more children in developing countries are successfully immunized, in addition to the clear life saving benefits, the people and governments of those countries will incur lower costs by preventing vaccine-preventable diseases instead of treating them.

Immunization protocols vary by region depending on the diseases prevalent there. Under some current childhood immunization protocols such as those used in the Cusco region of Peru for example, between birth and age 4, babies are scheduled to receive 10 different vaccinations in the form of 20 total shots. In other regions, children may be scheduled to receive more or fewer than 10 different vaccinations. For example, in the Amazon region of Peru as compared to the Cusco region, children are currently scheduled to more vaccinations to account for certain tropical diseases. The majority of the vaccines are given in a series of two or three shots. Each shot is scheduled to be administered on a particular date following the baby's birth, and often multiple different vaccines are administered on the same day.

However, for a variety of reasons, children in developing countries are often unable to successfully complete an immunization program. Immunization problems in developing countries include parents not knowing how many vaccines their child needs, how many and which vaccines their child has received, when and/or where the next vaccination is scheduled to be given, and the exact age of their child, among other challenges.

Thus, despite the fourth UN Millennium Development Goal to reduce the under-five mortality rate by two-thirds by 2015, which includes "ensuring full coverage of immunization programs", children in developing countries continue to experience lack of immunizations or incomplete immunizations.

For these and other reasons, there remain needs for improved and/or alternative methods and systems for tracking whether one or more medical-related events have occurred. The present invention is addressed to those needs.

SUMMARY

The present invention provides, in certain aspects, unique methods and systems for tracking occurrence and non-occurrences of medical-related events.

In one particular embodiment, the invention provides a method for tracking whether one or more medical-related events have occurred at a particular time or during a particular time interval. As part of this method, a band of material is provided which is capable of being worn about the body of a patient. There are multiple, separately-identifiable regions along the band including at least a first region and second region. The first region corresponds to a first particular time or first particular time interval, and the second region corresponds to a second particular time or second particular time interval. The method further includes indicating that a first medical-related event has occurred at the first particular time or during the first particular time interval which includes removing a segment of material from the first region, and indicating that a second medical-related event has occurred at the second particular time or during the second particular time interval which includes removing a segment of material from the second region. At least one of the medical-related events can be or involve the administration of a drug or therapy to the patient. Illustratively, in one preferred embodiment, the first medical-related event is the administration of a first dose of a first medicament to the patient, and the second medical-related event is the administration of a second dose of that same medicament to the patient.

In another aspect, the present invention provides a medical device for tracking whether one or more doses of at least one medicament have been administered to a patient. This particular device comprises an article which is capable of being worn about the body of a patient and which includes a length of flexible material which can provide a loop to be placed around a body part of the patient. The flexible material along the loop includes a plurality of predetermined removable segments which are each removable from the length of flexible material for indicating whether a particular medicament or dose of a medicament has been administered to the patient. As one example, the medical device might be specifically adapted to be worn about a wrist or ankle of the patient. With regard to the predetermined removable segments, they might have a reduced thickness relative to other portions of the length of flexible material and/or the length of flexible material might otherwise incorporate weakened portions of the flexible material that are adapted to facilitate predictable removal of the predetermined removable segments along predictable paths dictated by the weakened portions. This and some other inventive devices can be configured for tracking the administration of multiple different medicaments, e.g., one, two, three, four, five, six or more medicaments, to a patient.

Another aspect of the invention provides a method for tracking the administration of one or more medicaments to a patient. As part of this method, an article is provided which is capable of being worn about the body of a patient. The article includes a first portion that has relevance to the administration of a first dose of a medicament to the patient, and a second portion that has relevance to the administration of a second dose of the medicament to the patient. This method further includes indicating the administration of the first dose of the medicament to the patient which includes modifying the first portion in a generally predetermined fashion, and indicating the administration of the second dose of the medicament to the patient which includes modifying the second portion in a generally predetermined fashion. Illustratively, modifying the first portion might involve modifying the orientation or shape of the first portion, for example, by removing part of the first portion.

A further embodiment of the invention provides a method for tracking the occurrence of one or more medical-related events. As part of this method, an article is provided which is capable of being worn about the body of a patient. This method further includes indicating the occurrence of a first medical-related event that has relevance to a first portion of the article. Indicating the occurrence of the first medical-related event includes modifying the orientation or shape of the first portion. This first portion might be or include a generally flat, flexible segment of material where modification of the segment might involve, for example, removing and discarding a piece of the segment (e.g., an interior piece of the generally flat, flexible segment). In one preferred embodiment, the generally flat, flexible segment is outfitted with pre-manufactured weakened portions which are adapted to facilitate predictable removal of the piece along a predictable path dictated by the weakened portions. In further embodiments, one or more additional medical-related events are tracked with such an article. For example, the article may have a second portion having relevance to a second medical-related event, and a user can indicate the occurrence of the second medical-related event, e.g., by modifying the orientation or shape of the second portion. With such a device, the first and second medical-related events might be the same general event but occurring at different times (e.g., the administration of a first and second dose of a particular drug, first and second applications of a particular medical therapy, the performance of a particular medical test and a repeat to that test, etc.). Alternatively, as one more example, the first medical-related event might be the administration of a first drug to the patient at a particular time or during a particular time interval, and the second medical-related event might be the administration of a second, different drug to the patient at a particular time or during a particular time interval, whether the timing of the administration of the second drug is the same or different than the timing of the administration of the first drug.

Yet another embodiment of the present invention provides a method for tracking the occurrence of one or more medical-related events. As part of this method, an article is provided which is capable of being worn about the body of a patient. This method further includes indicating the occurrence of a first medical-related event having relevance to a first region of the article which includes removing a first portion of the first region. Although not necessary to broader aspects of this article, the removed portion might be one that was pre-established by the manufacturer to make the portion readily removable from the article, for example, where weakened portions are incorporated into the article to facilitate a generally predictable removal of the portion from the article. In some preferred forms, the article is outfitted such that the occurrence of a second medical-related event which also has relevance to the first region of the article is indicated, e.g., by removing a second portion of the first region. With such an article, as one example, the first medical-related event might be the administration of a first medicament, and the second medical-related event might be the administration of a second medicament. In this regard, the first portion and the second portion might be differently shaped with the shape of the first portion having relevance to the first medical-related event and the shape of the second portion having relevance to the second medical-related event. As another illustrative example, in some other preferred forms, the article might be outfitted such that the occurrence of a second medical-related event which has relevance to a second region of the article is indicated by removing a first portion of the second region. With such an article, as one example, the first medical-related event might be the administration of a first dose of a drug, and the second medical-related event might be the administration of a second dose of the same drug.

In another aspect, the invention provides a method for tracking the occurrence of one or more medical-related events. As part of this method, an article is provided which is capable of being worn about the body of a patient (e.g., around an ankle or wrist of the patient). This method further includes indicating the occurrence of a first medical-related event having relevance to a first portion of the article which includes modifying the first portion in a generally predetermined fashion. Such a modification might involve removing part of the first portion, for example, a less-than-full amount of the first portion (e.g., where the first portion incorporates a series of pre-manufactured disruption points that define a particular shaped path along a surface of the article and which are designed to facilitate separation of material generally along this shaped path). The article might be designed so that such a removal creates an opening in a wall of the article (e.g., where the opening is substantially or completely surrounded by material of the wall). Alternatively, as another example, such a modification might involve the association of a separate, additional component with the first portion. Such a component can be associated with the first portion in any number of manners including, for example, by bonding, coupling, connecting, etc. the component to the first portion. As yet another example, such a modification might otherwise involve altering the shape of the first portion or altering its orientation with respect to other portions of the article.

In a further embodiment, the invention provides a wearable band for tracking whether one or more medical-related events have occurred. This band comprises a circumferential band of material that includes at least a first region and a second region along the band. The first region includes a first predetermined removable segment which has relevance to a first medical-related event, and the second region includes a second predetermined removable segment which has relevance to a second medical-related event. In one preferred form, the first predetermined removable segment has a first shape that corresponds to a first particular medical treatment or therapy, and the second predetermined removable segment has a second shape which is different to the first shape and which corresponds to a second particular medical treatment or therapy. With some of these bands, the first region might represent a first particular time or time interval, and the second region might represent a second particular time or time interval that is different from the first particular time or time interval.

In a further embodiment, the invention provides a medical article which is capable of being worn about the body of a patient for tracking the administration of one or more medicaments to the patient. This article comprises a wearable device which includes a band of material (e.g., a generally flat band of material) that incorporates a plurality of removable segments that are removable from the band without reducing the length of the band. Each of the removable segments has significance with regard to whether a particular medicament or dose of a medicament has been administered to the patient. While not necessary to broader aspects of the article, the removable segments might be fixedly attached and detachable from the band.

In a further embodiment, the invention provides a method for tracking the occurrence of one or more medical-related events. As part of this method, a circumferential band of material is provided which is capable of being worn about the body of a patient. The band includes multiple, separately-identifiable regions along the band including at least a first region and a second region. Each of the regions has relevance to a particular medical-related event. This method further includes indicating the occurrence of a first medical-related event which includes altering the first region, and indicating the occurrence of a second medical-related event which includes altering the second region.

The above-described features, when suitably interchangeable or combinable between or among inventive embodiments, will be understood to be interchangeable or combinable in such a fashion.

Other objects, embodiments, forms, features, advantages, aspects, and benefits of the present invention shall become apparent from the detailed description and drawings included herein.

DETAILED DESCRIPTION

Figure 1:
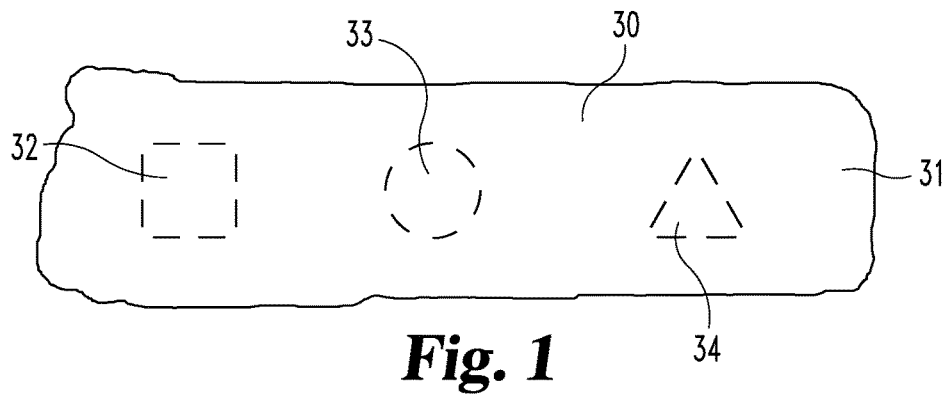
FIG. 1 is a partial view of a medical article according to one embodiment of the present invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

Inventive methods and systems, in some aspects of the present invention, will be used to track occurrences and/or non-occurrences of medical-related events, for example, to record whether one or more medical-related events have occurred at a particular time or during a particular time interval. Any suitable number of events may be tracked using such methods and systems, and the types and varieties of events that can be tracked are diverse. Examples include but are not limited to vaccine or other drug administrations, physical therapies, surgeries and other bodily treatments, tests, diagnoses, recording of symptoms and the like. In some preferred embodiments, these and/or other medical-related occurrences or events will be tracked using an article that can be worn about the body of a patient although a variety of non-wearable articles can be utilized as well. In some preferred forms, an inventive product will be specifically adapted to be worn about a wrist or ankle of a patient.

Illustratively, some inventive methods and systems involve the use of an article that is configured to be transformed or modified in a generally pre-specified fashion to indicate whether or not certain medical-related events have occurred. For example, such an article can be outfitted with a plurality of predetermined removable segments which are each removable from the article to indicate whether a particular medical-related event has occurred, e.g., to confirm that a particular medicament or dose of a medicament has been administered to a patient. With reference now to FIG. 1, shown is a partial view of a medical-related article 30 according to one embodiment of the present invention which includes a wall of material 31 that is perforated at specific locations along the wall to provide a first removable segment 32 generally in the shape of a square, a second removable segment 33 generally in the shape of a circle and a third removable segment 34 generally in the shape of a triangle. As one illustrative example, this type of article can be utilized in an inventive system which assigns each shaped segment to a specific drug that is to be administered to a patient, and which establishes that the removal of a particular shaped segment provides confirmation that the drug in question has been administered.

Figure 2A:
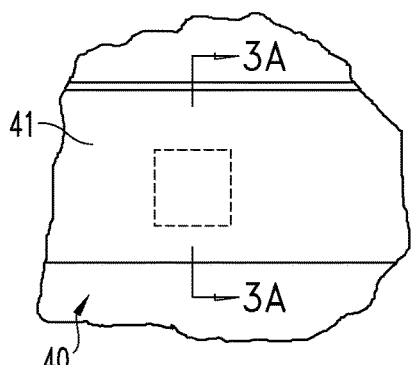
FIG. 2A is a partial, perspective view of a medical article with a square-shaped removable segment according to another embodiment of the present invention.
Figure 2B:
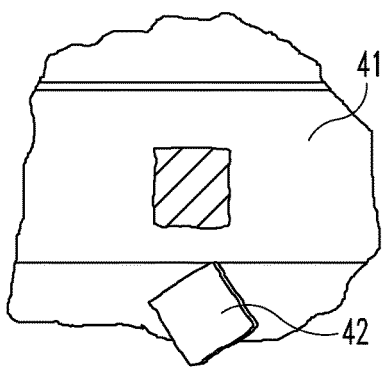
FIG. 2B shows the medical article of FIG. 3A with the square-shaped segment having been removed.

FIG. 2A is a partial view of an illustrative medical article 40 according to another embodiment of the present invention. Article 40 includes an elongate, generally flat band of material 41. In some preferred forms, such an elongate band will be formed with a flexible material such as silicone rubber. An elongate band of this sort can be adapted for use in a variety of the inventive methods and systems described herein. In this particular illustrative embodiment, band 41 incorporates a plurality of perforations which define a square-shaped region as shown. Such perforations facilitate removal of a generally square-shaped segment 42 from surrounding portions of the band as shown in FIG. 2B. Removal of the material creates a generally square-shaped opening in the band which in this case extends entirely through the band 41. Removing the segment reduces the weight of the band 41 but does not reduce the overall length of the elongate band.

Figure 3A:
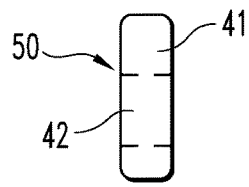
FIG. 3A provides a cross-sectional view of the band of FIG. 2A along the view line 3A-3A shown in FIG. 2A.
Figure 3B:
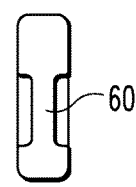
FIG. 3B provides a cross-section view of another inventive band.
Figure 3C:
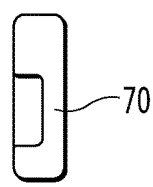
FIG. 3C provides a cross-section view of yet another inventive band.

When an inventive article incorporates a predetermined removable segment, these types of segments can be shaped and configured in a variety of manners. FIG. 3A is a cross-sectional view of the band 41 depicted in FIG. 2A, showing one illustrative way to perforate the material for facilitating removal of the square-shaped removable segment 42. As shown, slits or passages 50 are formed in the material and extend into the band from opposite sides of the band, e.g., from both the inner and outer surface of the band. Alternatively, such slits or passages could be formed into one side of the band only. When a perforation, opening, passage, etc. is formed in a wall of material, it can extend fully or partially through the wall. Various patterns and arrangements of perforations are contemplated in this regard as will be understood by those skilled in the art. FIGS. 3B and 3C provide cross-sectional views of material bands incorporating alternative pre-manufactured removable segments. In FIG. 3B, the band includes a region 60 having a reduced thickness relative to surrounding portions of the band. Region 60 is about 50% as thick as surrounding regions of the band. When a band or other inventive article includes a reduced-thickness region, the thickness of a particular region relative to other parts of the band can vary. The percentage of thickness reduction in some cases will be nearly 100%, and in other cases will only be a few percent. The percentage of reduction will generally be in the range of about 20% to about 80%, and in some cases will be in the range of about 30% to about 70%, and in some other cases will be more specifically in the range of about 40% to about 60%. In some inventive articles, a piece of material will include regions having a reduced thickness and will further incorporate perforations or the like to facilitate material removal.

Continuing with FIG. 3B, at the reduced-thickness location, there is material missing from opposite sides of the band, i.e., having a first square-shaped recess in the outer surface of the band and a second square-shaped recess in the inner surface of the band. Specifically, the reduced-thickness region 60 is substantially centered between opposite sides of the band. An alternative reduced thickness region 70 is shown in FIG. 3C where a shaped recess is formed in only one side of the band. By forming such a reduced thickness region, it is possible to facilitate a more effective and predictable removal of material from the article when such removal is desired (e.g., where a hole punch or similar device is used to remove at least a portion of, and in some cases all, the material remaining in the reduced-thickness region), although in some designs reducing the thickness of a region may be done for additional or alternative reasons such as to make a particular region more visible along the face of an article.

In some particularly preferred embodiments, an inventive article will be adapted to be worn about the body of a patient or will otherwise be capable of being mounted upon, carried upon or retained in association with the body of an individual. When an inventive article is of this type, it can exhibit a variety of constructions and configurations as discussed elsewhere herein. Examples of products that can be made to incorporate aspects of the present invention include but are not limited to products that are wearable upon and/or around an arm, wrist, finger, leg, ankle, toe, head, neck, chest or waist of an individual. Such articles can be formed with one or more of a variety of materials including synthetic polymeric and/or metallic materials. In some forms, a wearable article will be retained in association with a body part by forming a loop of material that extends partially or fully around the body part. When an article includes a loop having a closed circumference, this sort of loop might be provided by a single, uninterrupted loop of material (e.g., a single-piece, flexible polymer band that is formed within a mold and retains a generally annular shape). In alternative article embodiments, a substantially closed loop configuration will be attainable using article constructions similar to those found in bracelets, belts, necklaces, etc. Illustratively, an elongate band having opposing ends can be arranged into a substantially closed loop configuration and then generally held in that condition, for example, by releasably engaging or connecting different regions (e.g., end portions) of the band. A connection or engagement between parts of an elongate article to form a loop can be accomplished using various forms of buckles, clasps, one and multiple-part coupling mechanisms, adhesives and other bonding agents, by chemically or thermally fusing materials together and/or crimping overlapping materials.

Figure 4:
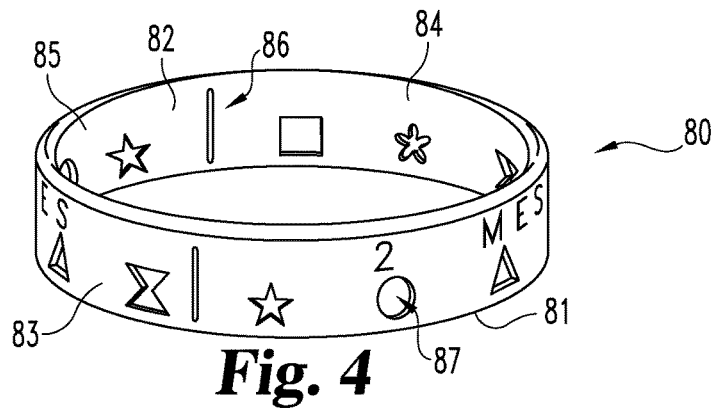
FIG. 4 is a perspective view of a wearable band according to one embodiment of the present invention.

Methods and systems, according to some aspects of the present invention, provide users with an ability to effectively track and verify whether one or multiple medical-related events have (or have not) occurred at a particular point in time, or across multiple points in time. In some particularly preferred embodiments, inventive methods and systems will be utilized to track whether multiple different drugs have been administered to a patient at different points in time. Illustratively, with reference now to FIG. 4, shown is a medical article 80 according to another embodiment of the present invention which includes an elongate band of material 81 having an annular configuration. The annular band has an inner face 82 and an outer face 83 which are provided by a generally flat, flexible piece of material. The band has an identifiable first region 84 that is separated from an identifiable second region 85 by dividing lines 86.

Spaced around the circumference of the band 81 are multiple shaped openings 87 which are the result of material having been removed from the band at those locations. Shaped openings in first region 84 include a star, circle, triangle, hour glass, clover and square. Second region 85 includes the same group of shaped openings except for the clover and square. Illustratively, the incorporation and removal of predetermined removable segments such as those described above in relation to FIGS. 1A-3C might be used to provide such openings, or alternatively, an inventive system might further provide a hole punch or similar material-removal device for removing material from an article such as band 81. For example, a hole punch might be used to form openings like the various shaped openings shown in FIG. 4, or it could be used to form a smaller opening (e.g., a circular opening) within a designated punch area like the square-shaped areas shown in FIGS. 3A-C, just to give a few examples. Accordingly, less material than the entire square-shaped areas of FIGS. 3A-C or the circular areas of FIG. 9 could be removed by a hole-punching or similar operation. In this regard, a hole punch-type device might be used any time material is to be removed from one of the articles disclosed herein, even when the article incorporates additional features such as perforations, reduced-thickness regions, etc. to facilitate material removal. When a hole punch-type device is used, various markings, indentations, reduced-thickness regions, protruding portions or regions, color combinations (e.g., corresponding to the shapes), etc. can be used along the article (e.g., as shown in one or more of the Figures herein) to direct the user where to generally execute a punch-out operation to signify that a particular medical-related event has or has not occurred. Thus, in some embodiments, the occurrence of a particular medical-related event will be confirmed by performing a punch-out operation generally at a particular location on an article and/or by punching out a particular shape or particular-sized opening from the article.

When one part of an article is to be removed from another part of the article, for example, as shown in FIG. 4 where multiple shaped segments have been removed from the article, with some of these designs, material of the article will incorporate one or more adaptations for facilitating separation of one material segment from another. Illustratively, a material can incorporate scores, thinner portions, and other openings and non-openings that weaken structurally a portion of the material to facilitate a tear-away operation, punch-out operation or disrupting material therealong with scissors, pliers, knife, etc. in removing one part of the material from another. Such a weakened portion may include any suitable means for facilitating tearing, cutting or breaking along the area. In certain beneficial forms, a segment is controllably separable along a particular grouping of weakened portions in the material, e.g., along a plurality of weakened portions forming a generally straight or curved line. These types of adaptations can be incorporated into an article in a variety of ways. Illustratively, in certain embodiments, an article will be originally constructed (e.g., in a mold, extruded, etc.) with weakened portions already incorporated into the article. However, when weakened portions are incorporated into an already-constructed article (e.g., into an existing silicone rubber member), such adaptations can be provided using a variety of techniques and instruments, for example, using lasers such as in laser cutting or etching, or employing any number of other tools or instruments. Forming these types of adaptations may or may not involve eliminating small portions of material from the article.

Continuing with FIG. 4, article 80 finds a particular use as a medical band for tracking the administration of childhood vaccines. For example, under some current childhood immunization protocols, between birth and age 4, babies are scheduled to receive multiple different vaccinations. The majority of the vaccines are given in a series of two or three shots. Each shot is scheduled to be administered at a particular time following the baby's birth, and often multiple different vaccines are administered on the same day. Table 1 immediately below shows data for a 20-shot immunization schedule that is currently being used in the Cusco region of Peru, and includes the Spanish names of the different vaccines and when, following birth, they are supposed to be administered to the child. Because immunization protocols vary by region depending on the diseases prevalent there, it will of course be understood that inventive articles can be adapted to track immunization protocols involving more or fewer than 10 vaccines or 20 total shots. Where tropical diseases are prevalent such as in the Amazon region of Peru, for example, children are currently scheduled to receive more than 20 total shots. The World Health Organization (WHO) has a list of vaccines all children should receive, and countries can add others depending on the level of risk for a certain disease. Currently, six is the minimum number of vaccines all children should receive according to the WHO.

TABLE 1

A Childhood Vaccine Schedule

| Vaccine | Month Given |
| --- | --- |
| BCG | 2 |
| HVB | 2 |
| Pentavalente | 2, 4, 6 |
| Antipolio | 2, 4, 6 |
| Neumococo | 2, 4, 6 |
| Rotavirus | 2, 4 |
| Influenza | 7, 8 |
| SPR | 12; 4 years |
| Antiamarilica | 12 |
| DPT | 18; 4 years |

Accordingly, for the above immunization protocol, an inventive method or system might utilize a band like that shown in FIG. 4, which can be outfitted with a total of ten removable, shaped segments, to track the administration of the first ten shots, i.e., doses of BCG, HVB, Pentavalente, Antipolio, Neumococo and Rotavirus scheduled to be delivered in the second and fourth months after birth. While not necessary to broader aspects of the invention, first region 84 corresponds to a time period occurring 2 MESES (meaning 2 months in Spanish) after the child selected to wear the article was born. Second region 85 corresponds to a time period occurring 4 MESES after the child was born. Thus, in one illustrative system, the clover-shaped segment can symbolize the BCG vaccine, the square-shaped segment can symbolize the HVB vaccine, the star-shaped segment can symbolize the pentavalente vaccine, the circular-shaped segment can symbolize the anitpolio vaccine, the triangular-shaped segment can symbolize the neumococo vaccine and the hour glass-shaped segment can symbolize the rotavirus vaccine. With such a system, it is possible to reference the article to determine things such as when to seek further vaccinations following the birth of the child, how many vaccinations a child will receive at a given time, and which vaccines are being administered at a given time, etc. Thus, the article of FIG. 4, where portions of the band have already been removed to form the multiple shaped openings 87, represents the completion of the first ten shots of the illustrative 20-shot protocol. While not necessary to broader aspects of the invention, preferably the band will be constructed such that it would be very difficult for the user to remove the removable segments by himself or herself. In an alternative embodiment, rather than a band being marked with 2 MESES and 4 MESES at the top, it could instead provide less information at the top (e.g., having only the numerical markings 2 and 4) or even provide somewhat more customized information or instructions, e.g., by listing the actual names of the months (e.g., February and April) a child is to receive further vaccinations, and optionally include even further detail for the user such as "Come to clinic in February", etc. With this sort of band, the caregiver would not need to know the age of the child as long as they knew the month of the year. Nonetheless, in some embodiments, the birth date of the child and/or other child-specific data will be marked onto the band or will otherwise be associated with the band for reference purposes, e.g., to be used in conjunction with other information on the band to determine when a vaccine is to be administered. In this regard, a band or other inventive article can be marked or otherwise modified in a variety of ways to indicate the user's name, birth date or some other user-specific information for reference purposes. Illustratively, a marking showing a child's name or birth date might be used instead of, or in addition to, one or more of the dividing lines 86, and in this regard, it will be understood that any suitable indicia can be used to indicate a division between regions on an article.

Using such a protocol, the 20 shots can be distributed over one or more bands, and in some cases preferably over two, three, four or more bands. In some particularly preferred embodiments, an article will be constructed to be generally safe for children, soft, flexible, and in some forms adjustable. Some of these bands will be durable enough to hold up over months or years of use. In one inventive system, two bands are used to complete the 20-shot protocol. After the first band (e.g., capable of tracking the first 10 shots) has been used, the child would exchange it for another one or more bands for tracking administration of the remaining shots. In one illustrative system, a child would wear one band through the sixth month, with 13 shots on that band and 7 on a second band. Other suitable single- and multi-band sets can be used for 20-shot protocols and other-than-20 shot protocols as discussed elsewhere herein.

Figure 10A:
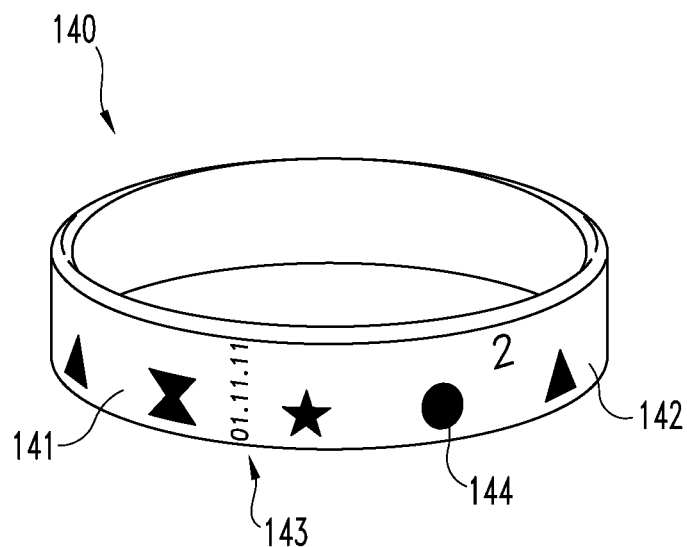
FIG. 10A is a perspective view of a wearable band according to another embodiment of the present invention.
Figure 10B:
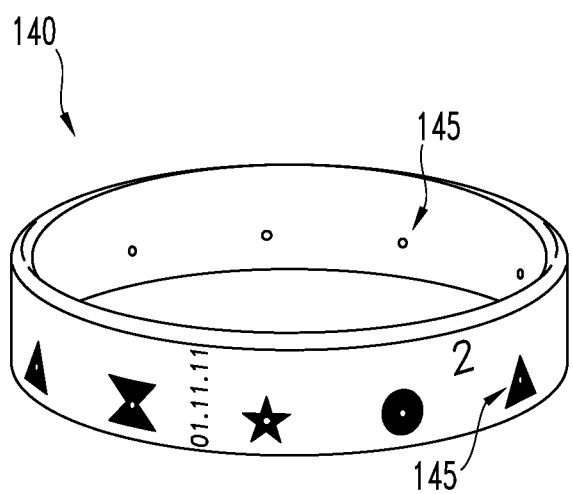
FIG. 10B is a perspective view of a wearable band according to another embodiment of the present invention.

As discussed above, in some embodiments, the occurrence of a particular medical-related event will be confirmed by performing a punch-out operation at a general location on an article and/or by punching out a particular shape or particular-sized opening from the article whether or not the article includes adaptations (e.g., perforations, reduced-thickness regions, etc.) to facilitate material removal. Illustratively, in the FIG. 1 article just to give one example, the square, circular and triangular areas, rather than being identifiable only by perforations in the material, might alternatively or additionally include colorings, markings or other indicia to help identify the specifically-shaped regions. In some forms, these various shapes will be made visible at least by painting or otherwise drawing them on the article, and a hole punch can be used to remove all or a portion of the visible shape. Such features could be applied to any of the articles disclosed herein. For example, FIGS. 10A and 10B show an annular band 140 that is similar to that shown in FIG. 4, and which can be used to track the first ten shots of the 20-shot protocol described in relation to FIG. 4. The outer face of the band includes an identifiable first region 142 that is separated from an identifiable second region 141 by indicia 143 representing the birth date (i.e., "01.11.11" or Jan. 11, 2011) of the child being immunized. First region 142, which includes the number "2" at the top, corresponds to a time period occurring 2 months after the child selected to wear the article was born. Second region 141, which includes the number "4" at the top but is not visible in FIGS. 10A and 10B, corresponds to a time period occurring 4 months after the child was born. Alternatively, the band could say "Return in 2 months" or equivalent and "Return in 4 months" or equivalent in the respective first and second regions, or "Return 03.11.11" or equivalent and "Return 05.11.11" or equivalent in the respective first and second regions.

Like FIG. 4, various shapes are identifiable around the circumference of the band 140, except that in this case the shapes (e.g., circular shape 144) are only drawn or painted onto the outer face of the band, and this regard, the entirety of the band has essentially the same thickness. There are no pre-manufactured disruptions points, reduced-thickness regions, etc. to indicate the various shapes although such features might additionally be included in alternative embodiments. Shaped markings in first region 142 include a star, circle, triangle, hour glass, clover and square (with only the first three shapes of first region 142 being visible in FIGS. 10A and 10B). Second region 141 includes the same group of shaped openings as first region 142 except for the clover and square; only the triangle and hour glass of second region 141 are visible in FIGS. 10A and 10B. Thus, when the rotavirus vaccine has been administered on or around the 2-month date according to the above-described protocol, a small hole can be punched (e.g., using a 1/16" hole punch) in the band in the area of the hour glass shape. FIG. 10A shows the band with no holes punched, while FIG. 10B shows the band after a small hole 145 has been punched in each of the 10 shapes to indicate that all 10 corresponding vaccine doses have been administered. Additionally, it should be understood that the shapes shown in FIG. 4 are merely illustrative, and that shapes, symbols, etc. can be chosen to be relevant to the culture in which an article will be used. Color, shapes, symbols, etc. can be aesthetically pleasing, gender-specific and/or culturally relevant so that users and caregivers are more likely to want to use them. As just some examples, portions of an article can be in the general shape of animals, local TV characters, foods, sports equipment, popular toys, etc. Any such markings or features can vary by country or region.

Figure 11A:
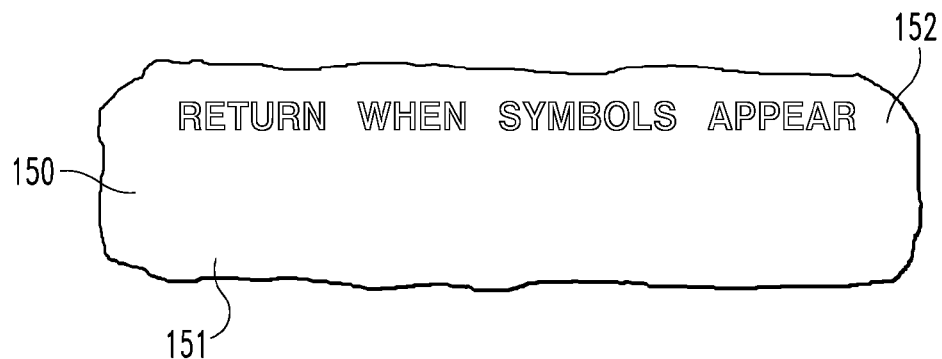
FIG. 11A is a partial view of a medical article according to one embodiment of the present invention.
Figure 11B:
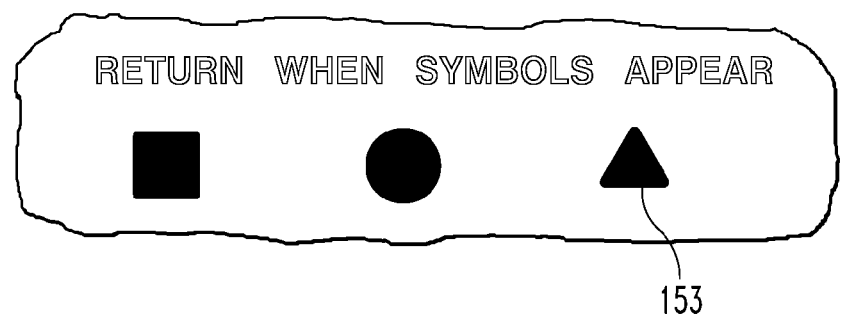
FIG. 11B is a partial view of the medical article of FIG. 13A.

Additionally, some inventive methods and systems will utilize an article that can signal to or otherwise notify the user that a medical-related event is due to occur, alert the user to seek further medical assistance, provide helpful information about a medical-related event to the user, provide timing information about a medical-related event, and the like. For example, such an article can be outfitted with a visible and/or audible notification system that can be programmed or otherwise set to notify the user about an event or otherwise provide information to the user. Many such systems that include built-in timing mechanisms are already known in the art and can be incorporated into any of the articles disclosed herein. These include but are not limited to incorporation of microchips and/or other electronic components, use of materials that through a chemical reaction or otherwise will change color, shape, size, etc. after a designated period of time to notify the user that a medical-related event is due to occur, or the like. One inventive article incorporating such a system is partially shown in FIGS. 11A and 11B. Article 150 provides a wall of material 151 which includes material portions that will change color after a period of time to notify the user to seek medical treatment. While the message "Return When Symbols Appear" is optional and merely illustrative of the many types of messages that could be displayed, in this particular instance it is useful to help inform the user that it is time to act. Such notification systems can be used alone or in conjunction with any one or more of the other tracking features disclosed herein. FIG. 11B shows the article 150 after a certain period of time (e.g., a number of minutes, hours, days, weeks, months or years) where various symbols 153, which where previously invisible, now appear on the article to assist in the notification function of the article. Once notified, the user can then seek medical treatment, and the article can be transformed or modified in any number of ways as disclosed herein (e.g., hole punched) to indicate that the treatment has been received. Additionally, an embedded audible notification system could directly inform the user to "Return to clinic for further treatment", etc.

Figure 12:
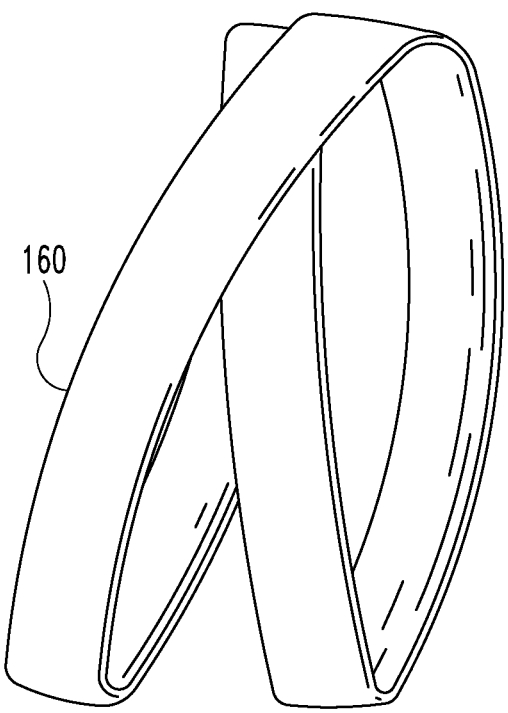
FIG. 12 is a perspective view of a wearable band according to another embodiment of the present invention.
Figure 13:
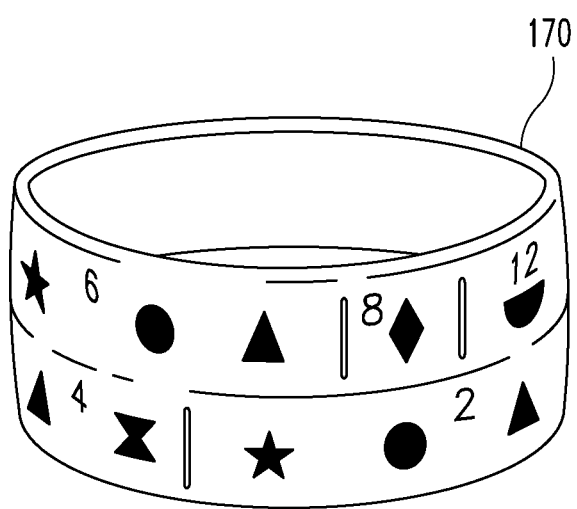
FIG. 13 is a perspective view of a wearable band according to another embodiment of the present invention.

Many suitable single- and multi-band sets can be used for tracking immunizations and other medical-related events. Illustratively, FIG. 12 shows another band 160 that can incorporate any one or more of the medical tracking features disclosed herein. With two loops of material, band 160 provides roughly double the surface area of a similar band having only one loop of material, and relative to such a single-loop band, might be used to track a greater number of events, and in some instances an entire immunization protocol having up to 20 or more individual shots. FIG. 13 shows a single band 170 that is similar to that shown in FIG. 10A except that it is about twice as wide and thus can more easily track the entire 20-shot immunization schedule shown in Table 1. There are two rows of shapes with at least some part of the 2, 4, 6, 8 and 12-month regions being visible in FIG. 13. As discussed elsewhere herein, the various shapes and regions can be arranged in any number of ways along the band.

In some forms, a key card that lists the names of the vaccines next to their corresponding symbols can be used with an article, for example, by a nurse administering the shots to the child, or by a parent or caregiver. Once a shot for a vaccine has been given, the nurse can refer to the key and then make the corresponding modification to the article, e.g., punch out a corresponding shape on the article. For example, if a baby is scheduled to receive "Vaccine A" in two shots given at two months and four months after birth, on an article in a "2 months" or equivalent region, a removable segment corresponding to Vaccine A can be present. This same shape will also appear on the article in the "4 months" or equivalent region, to indicate that this particular vaccine will be given in two shots, two months apart. A caregiver will know that a child has completed a vaccine after all modifications corresponding to that vaccine have been made. A laminated card or poster might also accompany the article which might display things such as the name of each vaccine, its dosage schedule, and a brief explanation of what diseases it prevents, etc. Literature of this type might also, for example, display how a vaccine generally works for educational purposes. To reinforce use of the article, the poster could also list the number of months after birth the caregiver should wait to bring a child back for a shot of a given vaccine.

The various illustrative embodiments shown and described herein demonstrate how, as part of an overall system for tracking occurrences and/or non-occurrences of medical-related events, an inventive article itself can be outfitted with varying degrees of accompanying information and detail that relate to the events being tracked. The level of detail provided on a particular inventive article can be varied as desired to suit a particular medical application, setting or patient. Accompanying detail in this regard can include but is not limited to various indicia, markings, physical features of the article, the use of various colors including using combinations of colors to differentiate between or among regions of an article, events to be tracked, etc. Nonetheless, it will be understood that a goal of some inventive embodiments will be to minimize the amount of accompanying information or detail appearing on the article itself.

Figure 5:
FIG. 5 is a partial view of a medical article according to another embodiment of the present invention.

FIG. 5 is a partial view of another illustrative article 90 that can be utilized in accordance with the present invention for medical-related purposes. The band includes a series of optional vertical markings or indicia which generally separate adjacent regions along a surface of the article. Within each of the separately-identifiable regions is a removable segment generally in the shape of one or more letters which correspond to one of the days of the week—"M" for Monday, "T" for Tuesday, "W" for Wednesday, "R" for Thursday, "F" for Friday, "Sa" for Saturday and "Su" for Sunday. In an illustrative manner of using such an article for medical-related purposes, the article, whether configured as a wearable article or an article that is not necessarily configured to be worn by the patient, could be distributed to the patient along with a medicine that is ordered to be taken once per day for seven days. After taking each day's dose, the patient would remove the corresponding removable segment (e.g., by punching it out with a pen) to confirm that she has taken the dose in question. A similar article could be outfitted with a fewer or greater number of removable segments as needed to suit a particular application or patient. In one preferred embodiment, the article could be one that is capable of being worn about the body of a patient, e.g., as a necklace or bracelet or in conjunction with such an item. In other preferred embodiments, the article could be associated with or form part of a container for housing the medicine in question, or could be a card or similar item distributed with the medicine. Article 90 is yet another illustrative example of how an inventive article might utilize one or more defined removable segments (e.g., in the shape of letters, words, numbers, or other shapes, etc.) employed about the article to provide information about, or to allow information to be provided about, one or more medical-related occurrences or non-occurrences being tracked with the article. Optionally, the article also could include the starting date for the doses and/or other user-specific information.

A large and diverse number of medical-related events and occurrences can be tracked or recorded using some of the specific methods and systems disclosed herein. Such things include but are not limited to indicating whether one or more rounds of a medical treatment, therapy, surgery, etc. have been performed on the body of a patient, indicating whether one or more doses of a medicament or drug have been administered to a patient, indicating whether one or more medical-related tests have been performed on a patient and/or indicating whether one or more medical-related diagnoses have been made in regard to a patient. In some preferred embodiments, inventive methods and systems will incorporate a chronological component to provide additional detail about the timing of medical-related events which have or have not occurred.

Figure 6:
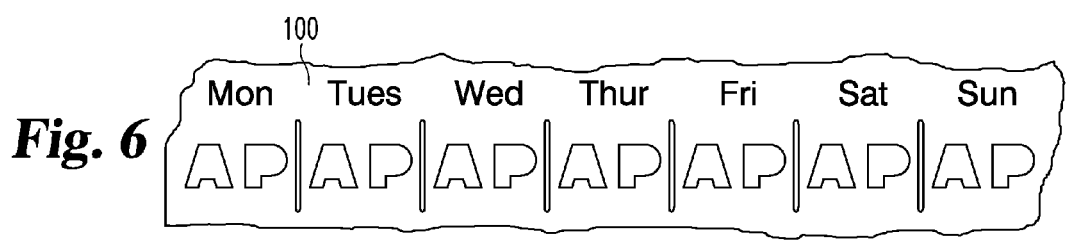
FIG. 6 is a partial view of another inventive medical article.

FIG. 6 is a partial view of another illustrative article 100 that can be utilized in accordance with the present invention for medical-related purposes. The band includes a series of optional vertical markings or indicia which generally separate adjacent regions along a surface of the article. Generally within each of the separately-identifiable regions is a marking which identifies that region as associated with one of the days of the week. Also within each region is a pair of removable segments, a first segment having a general outline of the letter "A" to represent the Latin phrase "ante meridiem" (before mid day) and a second segment having a general outline of the letter "P" to represent the Latin phrase "post meridiem" (after mid day). In an illustrative manner of using such an article for medical-related purposes, the article, whether configured as a wearable article or an article that is not necessarily configured to be worn by the patient, could be distributed to the patient along with a medicine that is ordered to be taken every 12 hours for seven consecutive days. After taking each 12 hour's dose, the patient would remove the corresponding removable segment to confirm that she has taken the dose in question.

Figure 7:
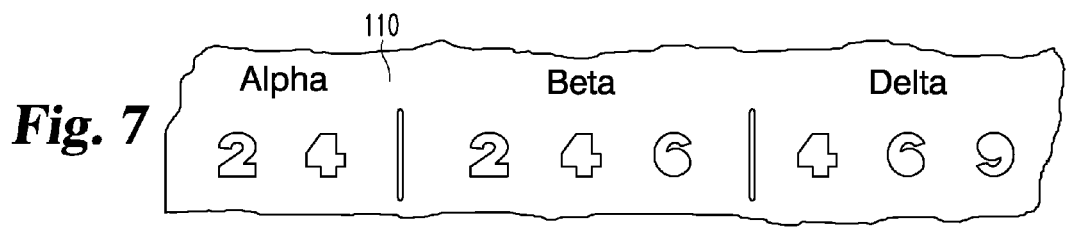
FIG. 7 is a partial view of another inventive medical article.

FIG. 7 is a partial view of another illustrative article 110 that can be utilized in accordance with the present invention for medical-related purposes. The band includes a series of optional vertical markings or indicia which generally separate adjacent regions along a surface of the article. Generally within each of the separately-identifiable regions is a marking (arbitrarily shown here as "Alpha", "Beta" and "Delta" for illustrative purposes) which associates that region with a particular medical-related object or event. Illustratively, the "Alpha" region might represent a first medicament to be administered to a patient on the second and fourth days of treatment. Accordingly, the "Alpha" region includes a first removable segment in the shape of the number "2" and a second removable segment in the shape of the number "4". Following this non-limiting example, the "Beta" region might represent a second medicament to be administered to the patient on the second, fourth and sixth days of treatment, and the "Delta" region might represent a third medicament to be administered to the patient on the fourth, sixth and ninth days of treatment such that the corresponding removable segments will be arranged and shaped as shown in FIG. 7.

Figure 8:
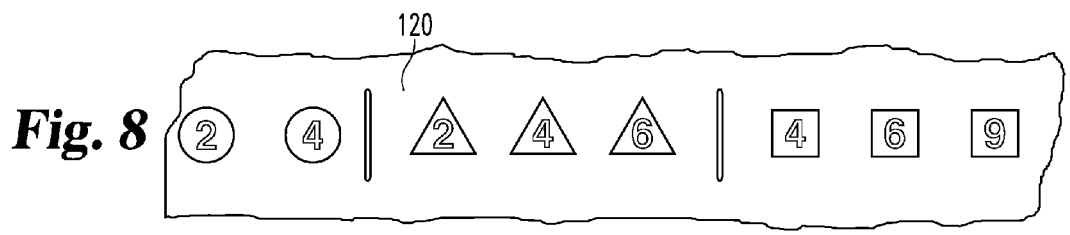
FIG. 8 is a partial view of another inventive medical article.

The article 120 depicted in FIG. 8 is similar to that shown in FIG. 7 except that instead of having each separately-identifiable region marked with a particular name or title (e.g., "Alpha"), the collection of removable segments in each different region are associated with a particular shape for that region. In this non-limiting example, the first region is associated with circular shapes, the second region is associated with triangular shapes and the third region is associated with square shapes. In this regard, it would be possible for the "circular" region to represent a first medicament, therapy, test, etc. to be administered to a patient on the second and fourth minutes, hours, days, etc. of treatment. Accordingly, the "circular" region includes a first circular removable segment marked with the number "2" and a second circular removable segment marked with the number "4". Following this non-limiting example, the "triangular" region might represent a second event to occur on the second, fourth and sixth minutes, hours, days, etc. of treatment, and the "square" region might represent a third event to occur on the fourth, sixth and ninth minutes, hours, days, etc. of treatment such that the corresponding removable segments will be arranged and marked as shown in FIG. 8.

A comparison of the articles in FIGS. 7 and 8 provides one illustrative example of how two inventive articles might be outfitted with different types or degrees of accompanying information or detail, yet the articles can be used to track the same or similar medical-related events. In FIG. 7, the different regions are marked with a particular name which might, for example, be the name of a particular drug to be administered to a patient. In FIG. 8, rather than have the name of the drug actually appear on the band, it could be established within the overall method or system that the circular-shaped segments represent the scheduled doses of the drug in question. As will be appreciated, the article in FIG. 8 could be further simplified by removing the number markings from the various removable segments if it was understood within the overall method or system when each different dose of each different vaccine was scheduled to be administered to the patient. In this regard, the level of accompanying information or detail on a particular article can be minimized, or an article can be provided with significant detail to convey information about the occurrence of one or more medical-related events, whichever is desired to suit a particular application, setting or patient.

Figure 9:
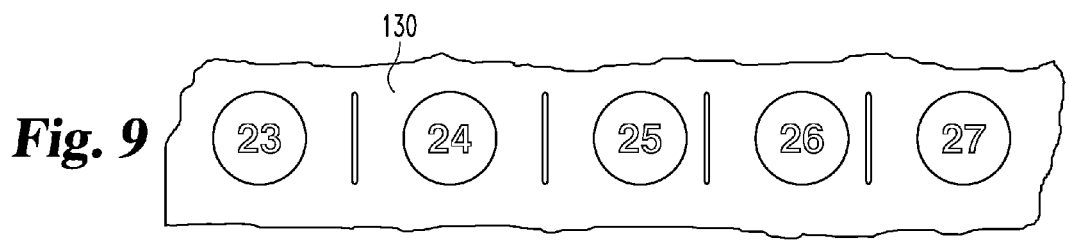
FIG. 9 is a partial view of another inventive medical article.

FIG. 9 is a partial view of another illustrative article 130 that can be utilized in accordance with the present invention for medical-related purposes. The band includes a series of optional vertical markings or indicia which generally separate adjacent regions along a surface of the article. Generally within each of the separately-identifiable regions is a circular-shaped removable segment that is marked with a number that associates that region or segment with a particular day of the month. In an illustrative manner of using such an article for medical-related purposes, the article, whether configured as a wearable article or an article that is not necessarily configured to be worn by the patient, could be distributed to the patient on the $23^{rd}$ day of a given month along with a medicine that is ordered to be taken once per day for five days. After taking each day's dose, the patient would remove the corresponding removable segment (e.g., by punching it out with a hole punch) to confirm that she has taken the dose in question. A similar article could be outfitted with a fewer or greater number of removable segments as needed to suit a particular application or patient. In one preferred embodiment, the article could be one that is capable of being worn about the body of a patient, e.g., as a necklace or bracelet or in conjunction with such an item. In another preferred embodiment, the article could be associated with or form part of a container for housing the medicine in question. The number markings on the circular segments in FIG. 9 may or may not be pre-marked from the manufacturer. In this regard, a "blank" article could be provided without the number markings, and a user (e.g., patient, physician, pharmacist, etc.) could customize the article in any desirable fashion, for example, by hand marking any desired numbers, letters, etc. onto the removable segments to correspond to one or more medical-related events to be tracked using the article. Additionally, the month and perhaps the year could be included along with any other information specific to the user or medical-related event to be tracked.

An inventive article, or portions thereof, can be constructed using one or more of a variety of materials including leather and a variety of synthetic polymers such as but not limited to polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

Suitable metallic materials may also be used in the construction of an inventive article, or a component thereof. Usable metallic material include but are not limited to stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy).

In additional embodiments, the present invention provides medical products that include means or devices as described herein for tracking occurrence and non-occurrences of medical-related events, and pamphlets, cards and/or other written or electronic materials including instructions and/or guidelines for using the means or devices to track, monitor or record occurrences and non-occurrences of medical-related events. The products can include the means or devices packaged together with written and/or electronic materials. Related embodiments of the invention include methods for distributing such means or devices, or otherwise conducting business, which include distributing such means or devices for tracking occurrence and non-occurrences of medical-related events, and also distributing information relating to the use of such means or devices for tracking occurrence and non-occurrences of medical-related events. Such information can be distributed packaged with the means or device, or separately, e.g., including information or instructions available on a communication network, including a global computer communication network such as the internet.

Any of the inventive articles disclosed herein can additionally or alternatively incorporate other information-providing means such as barcodes or similar markings and/or RFID chips or similar devices for identifying the user, providing medical-related information about the user, providing information about a specific medical-related event, tracking occurrences and non-occurrences of medical-related events specific to the user, etc. Such means can be used in conjunction with computers, scanners and other similar equipment for tracking, recording, analysis and other purposes, e.g., to provide a full or partial medical history of the user including information relevant to immunizations, etc. As just one example, article 150 includes an RFID chip 152 which is not visible in FIG. 11A because it is embedded within the wall of material 151. This or other information-providing means can be designed to remain with an article during its intended life cycle and/or such a means can be incorporated into one or more removable segments of an article such that the removal or non-removal of a particular segment will be recognized by a scanning operation, e.g., to automatically determine and record whether a corresponding medical-related event has or has not occurred.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A method for tracking the occurrence of one or more medical-related events, the method comprising:
   providing an article capable of being worn about the body of a patient, the article comprising
      a first portion having relevance to a first medical-related event of the patient, the first portion indicating the occurrence or non-occurrence of the first medical-related event, the first medical-related event being the performance of a first medical test on the patient at a first particular time or during a first particular time interval, and
      a second portion having relevance to a second medical-related event of the patient, the second portion indicating the occurrence or non-occurrence of the second medical-related event, the second medical-related event being the performance of the first medical test on the patient at a second particular time or during a second particular time interval different than the first medical-related event,
   modifying the orientation or shape the first portion to indicate the occurrence of the first medical-related event,
   modifying the orientation or shape the second portion to indicate the occurrence of the second medical-related event, and
   placing the article on the body of the patient.
2. The method of claim 1, wherein the first portion comprises a generally flat, flexible segment of material and the step of modifying of the first portion comprises removing and discarding a piece of the segment.
3. The method of claim 1, wherein the article comprises a band.
4. The method of claim 3, wherein the band is sized to be worn about at least one of a wrist and ankle of a patient.
5. The method of claim 3, wherein the band has a thickness, a height, and a diameter, and the height of the band is less than the diameter of the band.
6. The method of claim 1, wherein the article comprises a flexible polymer material.
7. A method for tracking the occurrence of one or more medical-related events, the method comprising:
   providing an article capable of being worn about the body of a patient, the article comprising a first region,
   indicating the occurrence of a first medical-related event having relevance to the first region of the article which includes removing a first portion of the first region using a hole punch, and
   placing the article about the body of the patient.
8. The method of claim 7, further comprising a step of indicating the occurrence of a second medical-related event having relevance to the first region of said article which includes removing a second portion of the first region.
9. The method of claim 8, wherein the first medical-related event is the administration of a first medicament, and the second medical-related event is the administration of a second medicament.
10. The method of claim 7, further comprising a step of indicating the occurrence of a second medical-related event having relevance to a second region of the article which includes removing a first portion of the second region.
11. The method of claim 10, wherein the first medical-related event is the administration of a first dose of a first medicament, and the second medical-related event is the administration of a second dose of the first medicament.
12. A method for tracking the occurrence of one or more medical events, the method comprising:
   providing an article capable of being worn about the body of a patient, the article comprising a first portion having relevance to a first immunization event,
   modifying the first portion to indicate the occurrence of the first immunization event to the patient, and
   placing the article about the body of the patient.
13. The method of claim 12, wherein the article has a second portion having relevance to a second immunization event; further comprising a step of modifying the second region to indicate the occurrence of a second immunization event.
14. The method of claim 12, wherein the step of modifying the first portion includes associating a separate, additional component at least partially with the first portion.
15. The method of claim 14, wherein the associating includes coupling or connecting to the separate, additional component to the first portion.
16. The method of claim 12, wherein the article is configured to be worn about at least one of an ankle, wrist, neck, and leg of the patient.

* * * * *